United States Patent [19]

Gauthier-Lafaye et al.

[11] Patent Number: 4,500,474
[45] Date of Patent: Feb. 19, 1985

[54] CARBONYLATION OF METHYL ACETATE

[75] Inventors: Jean Gauthier-Lafaye, Lyons; Robert Perron, Charly, both of France

[73] Assignee: Rhone-Poulenc Chimie de Base, Courbevoie, France

[21] Appl. No.: 387,467

[22] Filed: Jun. 11, 1982

[30] Foreign Application Priority Data

Jun. 12, 1981 [FR] France .................. 81 11787

[51] Int. Cl.$^3$ ............................. C07C 51/12
[52] U.S. Cl. .................................. 260/549
[58] Field of Search ............ 260/549; 560/232; 568/484; 562/517

[56] References Cited

U.S. PATENT DOCUMENTS 2,730,546 1/1956 Reppe et al. .............. 260/549
4,115,444 9/1978 Rizkalla .................. 260/549
4,189,441 2/1980 Braca et al. .............. 560/232

OTHER PUBLICATIONS

Clark, N. G., Modern Organic Chemistry (1964), Oxford Univ. Press. Publ., at p. 246.

Primary Examiner—Natalie Trousof
Assistant Examiner—L. Hendriksen
Attorney, Agent, or Firm—Burns, Doane, Swecker & Mathis

[57] ABSTRACT

Methyl acetate is carbonylated, advantageously to acetic anhydride, in a homogeneous liquid phase, in a virtually anhydrous reaction medium, in the presence of: (a) a cobalt source, (b) a ruthenium source, (c) an ionic iodide of the formula: $A^{m+}I_m^-$ in which $A^{m+}$ is a nitrogen group quaternary onium cation, an alkali metal or alkaline earth metal cation, or a lanthanide or actinide group metal cation, (c') if appropriate, a carboxylate of the formula: $A'^{n+}(OCOR)_n^-$, in which n is 1 or 2 and $A'^{n+}$ is defined as was $A^{m+}$, with $A'^{n+}$ and $A^{m+}$ either being the same or different, and R is an alkyl, aralkyl or aryl radical having a maximum of 8 carbon atoms, and (d) hydrogen, the total amount of halogen compounds present in the carbonylation reaction medium (expressed in gram atoms of halogen and designated by $X_T$) being such that the atomic ratio $X_T/(m.A^{m+}+n.A'^{n+})$ is less than or equal to 1.

20 Claims, No Drawings

CARBONYLATION OF METHYL ACETATE

BACKGROUND OF THE INVENTION

1. Field of the Invention

The present invention relates to the carbonylation of methyl acetate in a virtually anhydrous medium, and, more especially, relates to the carbonylation of methyl acetate in a virtually anhydrous medium, in the presence of a cobalt-based catalyst.

2. Description of the Prior Art

U.S. Pat. No. 2,730,546 describes the carbonylation of methyl acetate to prepare acetic anhydride, in the presence of a catalyst selected from among the cobalt complexes of the general formula:

$$[R_4A]_2CoX_4$$

in which X represents a bromine or iodine atom, A represents a nitrogen or phosphorous atom and R represents a lower alkyl radical, for example.

These complexes can be formed in situ by introduction into suitable reaction vessel of, firstly, a cobalt halide ($CoX'_2$) and secondly a quaternary ammonium (or phosphonium) halide ($R_4AX$). The formation of the subject complexes can thus be represented by the following reaction:

$$2(R_4AX) + CoX'_2 \rightarrow [R_4A]_2CoX'_2X_2.$$

However, the efficacy of these cobalt-based catalysts appeared to be relatively low. This type of process, the value of which is not contested in principle, has to date proven unacceptable on an industrial scale.

French Pat. No. 2,242,362 (corresponding to U.S. priority applications, Ser. No. 394,220 and Ser. No. 467,997, respectively filed on Sept. 4, 1973 and May 8, 1974the latter having issued as U.S. Pat. No. 3,904,134) describes a two-stage process for the preparation of acetic anhydride, in which, in a first step, methyl bromide or, preferably, iodide is carbonylated to provide the corresponding acetyl halide, such acetyl halide in turn being reacted with methyl acetate, in a second step, to provide acetic anhydride, which corresponds to the following reaction scheme, in the event that methyl iodide is the starting material:

Step 1:

$$CH_3I + CO \rightarrow CH_3COI$$

Step 2:

$$CH_3COI + CH_3COOCH_3 \rightarrow (CH_3CO)_2O + CH_3I.$$

As is readily apparent from this scheme, the methyl iodide, which is the starting material of step 1, is "regenerated" in step 2. Step 1 is advantageously carried out in the presence of a rhodium-based catalyst; step 2 would be assisted by the presence of lithium and/or chromium. Both steps would be assisted by the presence of lithium and/or chromium. Both steps can be carried out in one and the same reaction zone, which will then contain methyl iodide, methyl acetate, rhodium and, if appropriate, lithium and/or chromium, and even acetyl iodide, into which zone carbon monoxide will also be introduced.

U.S. Pat. No. 4,115,444 proposes an improvement to the technique described in the abovementioned French patent, which improvement consists in adding, to the reaction medium, an organic phosphorus or nitrogen compound in which the phosphorus or the nitrogen is trivalent, and confirms the potential value, in this reaction, of catalyst systems based on rhodium, or even palladium or iridium, and chromium.

French Pat. No. 2,303,788 (corresponding to U.S. priority applications Ser. No. 556,749 and Ser. No. 654,662, respectively filed on Mar. 10, 1975 and Feb. 5, 1976) reflects that the presence of a large amount of hydrogen in the reaction medium above described has a considerable influence upon the direction of the reaction. In fact, under these conditions, a mixture is obtained which contains a preponderant proportion of acetic acid and variable amounts of ethylidene diacetate, acetic anhydride and acetaldehyde.

The principal value of these processes employing catalysts based on rhodium, or even palladium or iridium, the systems based on the pair (rhodium/chromium) appearing to be the most active, essentially resides in the possibility which they present of obtaining acetic anhydride starting from methyl acetate, utilizing carbon monoxide partial pressures which are lower than those required in the earlier processes.

Nevertheless, the attempts to develop this type of process, even on a simple pilot plant scale, have encountered serious difficulties.

A first series of difficulties arises from the fact that the catalysts based on rhodium or palladium, or even iridium, which metals are extremely rare and expensive, are deactivated, in particular during the treatments required to recover the reaction product (or products). Because of the cost of these catalysts, it is essential to regenerate same. Furthermore, the conditions required to convert these metal compounds to catalytically active species in the carbonylation reaction are most frequently incompatible with those required to maintain the chromium-based co-catalysts in their active form in this same reaction. Still further, the losses of rhodium, for example, which seem to be unavoidable at the various points in an industrial plant, severely impair the economics of such a process.

A second series of difficulties is derived from the presence, required for the reaction to proceed well and for the stabilization of the rhodium, of large amounts of methyl (or acetyl) iodide, which involves significant risks of corrosion at the various points in an industrial installation. Furthermore, the methyl iodide and/or certain of its derivatives formed in the reaction medium are responsible for an unacceptable contamination of the reaction product (or products), which makes it necessary to carry out additional steps in order to remove the iodides whose presence in the reaction products proves to be undesirable. For obvious economic reasons, these iodine derivatives, which are present in large amounts not only in the products but also in various effluents originating from the reaction zone, must be recovered, and this involves additional treatment stages.

The various problems associated with this type of process, which are difficult to solve, will become more clearly apparent from French Pat. Nos. 2,438,023 and No. 2,438,024 (corresponding respectively to U.S. priority applications, Ser. No. 949,344 and Ser. No. 949,345, filed Oct. 6, 1978these applications having issued as U.S. Pat. Nos. 4,252,741 and 4,246,192, respectively) and U.S. Pat. No. 4,241,219.

Too, it is also well known that methyl acetate can be obtained by reacting acetic acid with methanol, it being possible for the acetic acid to be produced by the carbonylation of methanol and for the methanol in turn to be prepared by the hydrogenation of carbon monoxide. The reactions in question can be represented as follows:

$$CO + 2H_2 \rightarrow CH_3OH \quad (a)$$

$$CH_3OH + CO \rightarrow CH_3COOH \quad (b)$$

$$CH_3COOH + CH_3OH \rightarrow CH_3COOCH_3 + H_2O \quad (c)$$

The carbonylation of methyl acetate in a substantially anhydrous medium makes it possible to obtain acetic anhydride according to the following reaction:

$$CH_3COOCH_3 + CO \rightarrow CH_3CO-O-COCH_3 \quad (1)$$

Thus, the value of a process for the carbonylation of methyl acetate to yield acetic anhydride (1) is clearly apparent if reactions (a) to (c) above are also considered, since, overall, this sequence amounts to a process by which acetic anhydride is produced beginning from carbon monoxide and hydrogen.

Furthermore, cobalt being a common metal, its use in a process for the carbonylation of methyl acetate would be desirable. Nonetheless, to date the prior art has almost exclusively focused upon the rhodium based catalyst systems in such process.

SUMMARY OF THE INVENTION

Accordingly, a major object of the present invention is the provision of an improved process to carbonylate methyl acetate effectively, in a virtually anhydrous medium, in the presence of a cobalt-based catalyst system.

Briefly, the present invention features a process for the carbonylation of methyl acetate in a homogeneous liquid phase, in an essentially anhydrous medium, in the presence of:
(a) a source of cobalt;
(b) a source of ruthenium;
(c) an ionic iodide of the formula:

$$A^{m+}I_m^-$$

in which $A^{m+}$ is a cation selected from the group comprising the quaternary onium cations derived from the elements of the nitrogen group, the alkali metal cations, the alkaline earth metal cations, the cations of the metals of the lanthanide group and the cations of the metals of the actinide group, m being an integer equal to 1, 2, 3 or 4:
(c') if appropriate, a carboxylate of the formula:

$$A'^{n+}(OCOR)_n^-$$

in which n is equal to 1, 2, 3 or 4 and $A'^{n+}$ has the meaning given above for $A^{m+}$, with $A'^{n+}$ and $A^{m+}$ being the same or different, and R is an alkyl, aralkyl or aryl radical having a maximum of 8 carbon atoms; and
(d) hydrogen,
the total amount of halogen compounds present in the reaction medium (expressed in gram atoms of halogen and designated as $X_T$ hereinafter) is less than or equal to 1 being such that the atomic ratio $X_T/m.A^{m+} + n.A'^{n+}$).

DETAILED DESCRIPTION OF THE INVENTION

More particularly according to this invention, the subject carbonylation of methyl acetate is indeed quite notable in several respects. In fact, it has been found, totally unexpectedly, that the addition of a source of ruthenium and hydrogen to the reaction medium containing ingredients of the type (a), the type (c) and, if appropriate, the type (d) set forth above, makes it possible to prepare acetic anhydride, in particular, with an especially high hourly productivity, whereas, under the same reaction conditions, cobalt by itself possesses but mediocre carbonylating activity and efficacy in the reaction envisaged, and ruthenium by itself, under these same conditions, provides virtually no carbonylating activity whatsoever.

Without wishing to be bound to any particular theory or reaction mechanism, it would appear that the carbonylating activity must be attributed, in the present process, to the source of cobalt, which, under the reaction conditions, would be converted to a catalytically active species, the precise nature of which has not as yet been totally elucidated.

The second metal constituent of the subject catalyst system (the source of ruthenium), which itself possesses virtually no carbonylating activity, apparently serves only to increase the activity and/or the concentration of active cobalt species or its useful life, if appropriate. The reasons for this noteworthy influence is unknown, but could lie in a change in the oxidation state and/or the arrangement, or even in the nature, of the ligands of the central cobalt atom. Stated differently, the source of ruthenium would serve to facilitate the appearance and, if appropriate, the maintaining of the active form of cobalt in the reaction medium.

Furthermore, it too has been found, also totally surprisingly, that, in contrast to the direction of the prior art, the efficacy of the present process is not related to the presence of large amounts of methyl iodide. On the contrary, when methyl iodide is added upon carrying out the process of the invention, a considerable reduction in process efficacy is observed.

The precise reason for the adverse influence of methyl iodide, a phenomenon which is in total contradistinction to the teachings of the prior art, is unknown. Also without wishing to be bound to any particular theory or explanation, it is assumed that the methyl iodide, when it is present in considerable amounts, disturbs or disrupts the complex equilibria which would, in particular, cause the very high reactivity of the cobalt under the conditions described.

On the other hand, the carbonylating activity of the catalyst system above described is not related to the precise nature of the cobalt compound or compounds initially introduced. It is possible, within the scope of the present invention, to use any source of cobalt whatsoever which is capable of reacting with carbon monoxide in the reaction medium to provide cobalt carbonyl complexes. Examples of the typical sources of cobalt are finely divided cobalt metal, inorganic cobalt salts (nitrate, carbonate, halides, and the like) or organic salts, in particular the carboxylates. It is also possible to employ cobalt carbonyls or hydrocarbonyls and hydrotetracarbonylcobalt salts. Among the cobalt derivatives which are suitable for carrying out the process according to the invention, representative are the formate, the acetate and, more particularly, dicobalt octacarbonyl, lithium tetracarbonylcobaltate, sodium tetracarbonylcobaltate and methyltriphenylphosphonium tetracarbonylcobaltate.

The precise amount of cobalt employed in the reaction medium is not of fundamental importance. In general, the reaction is carried out with an amount of cobalt which is such that the concentration in the reaction medium, expressed in milligram atoms per liter (mg atoms/l), ranges from 0.1 to 200 and preferably ranges from 0.5 to 100 mg atoms/l.

One advantage of the present process is the fact that it is possible to obtain good results with a low cobalt concentration.

A source of ruthenium is also used to carry out the present process. The precise form in which the ruthenium is introduced into the initial reaction medium is also not of fundamental importance. Examples of typical sources of ruthenium are finely divided ruthenium metal, ruthenium carboxylates (in particular the acetate), ruthenium acetylacetonate and ruthenium carbonyls (in particular $Ru_3(CO)_{12}$).

The amount of ruthenium present in the initial reaction medium too is not of fundamental importance. In general, this amount will be such that the atomic ratio Ru/Co ranges from 0.005 to 25. For the present process to proceed well, the atomic ratio Ru/Co advantageously ranges from 0.02 to 10 and preferably from 0.2 to 5.

The process according to the present invention also requires the presence of an ionic iodide of the formula:

$$A^{m+}I_m^-$$

in which $A^{m+}$ and m are as defined above.

By the expression "quaternary onium cations derived from elements of the nitrogen group" there are intended cations formed from nitrogen, phosphorus, arsenic or antimony and from four identical or different, monovalent hydrocarbon groups, the free valency of which being borne by a carbon atom, each such group being bonded to the abovementioned element via said free valency, and it is furthermore possible for any two such groups to together form a single divalent radical.

Among these compounds, preferred are the quaternary phosphonium (or ammonium) iodides. The cations of these iodides are conveniently represented by the formulae (I) to (III) below:

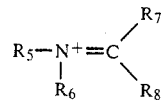
(I)

in which Q represents a nitrogen or phosphorous atom and $R_1$, $R_2$, $R_3$ and $R_4$, which can be identical or different, represent organic radicals, the free valency of which being borne by a carbon atom, it being possible, if appropriate, for any two of these various radicals to together form a single divalent radical.

More specifically, $R_1$, $R_2$, $R_3$ and $R_4$ are preferably linear or branched chain alkyl radicals, cycloalkyl radicals, aralkyl,(for example, benzyl) radicals or monocyclic aryl radicals, having at most 16 carbon atoms and can, if appropriate, be substituted by 1 to 3 alkyl radicals having from 1 to 4 carbon atoms, it being possible, if appropriate, for two of the radicals $R_1$ to $R_4$ to together form a single divalent alkylene or alkenylene radical containing 3 to 6 carbon atoms (for example, a tetramethylene or hexamethylene radical) and, if appropriate, comprising 1 or 2 ethylenic double bonds, and it also being possible for said radical to be substituted with from 1 to 3 alkyl substituents having from 1 to 4 carbon atoms.

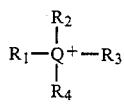

in which $R_5$, $R_6$, $R_7$ and $R_8$, which are identical or different, represent alkyl radicals having from 1 to 4 carbon atoms, it also being possible for one of the radicals $R_7$ or $R_8$ to represent hydrogen, and it being possible, if appropriate, for $R_7$ and $R_8$ to together form a single divalent alkylene radical containing from 3 to 6 carbon atoms, for example, a tetramethylene or hexamethylene radical; $R_6$ and $R_7$ or $R_8$ can together form a single divalent alkylene or alkenylene radical containing 4 carbon atoms and, if appropriate, comprise 1 or 2 ethylenic double bonds, the nitrogen atom then being included in a heterocyclic ring to form, for example, a pyridinium cation.

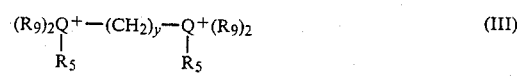

in which $R_5$ and $Q^+$ are as defined above, $R_9$, which can be identical to $R_5$, represents an alkyl radical having from 1 to 4 carbon atoms or a phenyl radical, and y is an integer ranging from 1 to 10 inclusive and preferably from 1 to 6 inclusive. The following are specific examples of quaternary ammonium iodides which are suitable for carrying out the present process: tetramethylammonium, triethylmethylammonium tributylmethylammonium, trimethyl-(n-propyl)-ammonium, tetraethylammonium, tetrabutylammonium, dodecyltrimethylammonium, benzyltrimethylammonium, benzyldimethylpropylammonium, benzyldimethyloctylammonium, dimethyldiphenylammonium, methyltriphenylammonium, N,N-dimethyl-trimethyleneammonium, N,N-diethyl-trimethyleneammonium, N,N-dimethyl-tetramethyleneammonium, N,N-diethyl-tetramethyleneammonium, N-methylpyridinium, N-ethylpyridinium and N-methylpicolinium iodides.

The following are specific examples of quaternary phosphonium iodides which are also suitable for carrying out the present process: tetramethylphosphonium, ethyltrimethylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri-(isopropyl)phosphonium, methyl-tri-(n-propyl)-phosphonium, methyl-tri-(n-butyl)-phosphonium, methyl-tri-(2-methylpropyl)-phosphonium, methyltricyclohexylphosphonium, methyltriphenylphosphonium, methyltribenzylphosphonium, methyl-tri-(4-methylphenyl)phosphonium, methyltrixylylphosphonium, diethylmethylphenylphosphonium, dibenzylmethylphenylphosphonium, ethyltriphenylphosphonium, tetraethylphosphonium ethyl-tri-(n-propyl)-phosphonium, triethylpentylphosphonium, ethyltriphenylphosphonium, n-butyl-tri-(n-propyl)-phosphonium, butyltriphenylphosphonium, benzyltriphenylphosphonium, (β-phenylethyl)-dimethylphenyl-phosphonium, tetraphenylphosphonium and triphenyl-(4-methylphenyl)-phosphonium iodides.

The precise nature of the quaternary ammonium or phosphonium cation is not of critical importance within the scope of the present invention. The selection from among such compounds is governed more by considerations of a practical nature, such as the solubility in the reaction medium, the availability and the convenience of use.

In this respect, the quaternary or phosphonium iodides represented either by the formula (I) in which any one of the radicals $R_1$ to $R_4$ is selected from among linear alkyl radicals having from 1 to 4 carbon atoms, or by the formula (II) or (III) in which $R_5$ (or $R_6$) is also an alkyl radical having from 1 to 4 carbon atoms, are particularly suitable.

Moreover the preferred ammonium iodides are those of which the cations correspond to the formula (I) in which all the radicals $R_1$ to $R_4$ are selected from among linear alkyl radicals having from 1 to 4 carbon atoms, and in which at least three of same are identical.

Likewise, the preferred quaternary phosphonium iodides are those of which the cations correspond to the formula (I) in which any one of the radicals $R_1$ to $R_4$ represents a linear alkyl radical having from 1 to 4 carbon atoms, the other three radicals being identical and being selected from among phenyl, tolyl or xylyl radicals.

The iodides of alkali metals, alkaline earth metals, metals of the lanthanide group and metals of the actinide group are also suitable for carrying out the present invention. The use of this type of iodide is preferred if it is desired to carry out the present process at a temperature below 160° C. and under a total pressure, at this temperature, of less than 100 bars or even of less than 80 bars. The alkali metal iodides, in particular lithium iodide, are more particularly preferred for carrying out the present process. However, for the reaction medium to be homogeneous in the event that iodides of this type are used, a solvent selected from among tetramethylenesulfone, N-methylpyrrolidone and monocarboxylic acid amides which are derived from acids having a maximum of 8 carbon atoms and in which the nitrogen atom contains two alkyl substituents having a maximum of 4 carbon atoms, should also be introduced into the reaction medium. This type of solvent is used in an amount of 5 to 90% (by volume) of the reaction medium, although higher or lower proportions can be used. For the invention to be carried out with good results, the solvent will represent, within this particular embodiment, from 10 to 60% by volume of the said reaction medium.

The amount of ionic iodide to be used within the scope of the present invention is generally such that the molar ratio $I^-/Co$ is greater than or equal to 5 and preferably greater than or equal to 10. No advantage is gained if this ratio exceeds a value of 200. The molar ratio $I^-/Co$ will advantageously be fixed at a value ranging from 15 to 150.

Also as above indicated, the present invention can also be carried out in the presence of a carboxylate of the formula:

$$A'^{n+}(OCOR)_n^-$$

in which n is equal to 1, 2, 3 or 4, $A'^{n+}$ has the meaning given above for $A^{m+}$, it furthermore being possible for $A'^{n+}$ and $A^{m+}$ to be identical or different, and R is an alkyl, aralkyl or aryl radical having a maximum of 8 carbon atoms.

This embodiment is quite advantageous within the scope of the present invention when using an alkali metal iodide or alkaline earth metal iodide or iodides of metals of the lanthanide group or actinide group. In fact, the carboxylates in question seem to limit the appearance in situ of methyl iodide (the adverse effect of which in the present process having already been pointed out), which can be formed by reaction of the said iodides with the methyl acetate (starting material) according to the equation given below for the particular case of lithium iodide, the formation of methyl iodide being greater when starting from lithium iodide than when starting from an equivalent amount of sodium iodide or potassium iodide (for example):

$$Li^+I^- + CH_3COOCH_3 \rightarrow CH_3I + Li^+(OCOCH_3)^-.$$

It is not necessary for the carboxylate $A'^{n+}(OCOR)_n^-$ to be derived from the same cation as the ionic iodide used. The carboxylate is advantageously an acetate.

It will be appreciated that certain acetates can be considered as the addition products of methyl acetate and a phosphine, an amine, an arsine or a stibine, according to the equation given for the particular case of triphenylphosphine for simplicity:

$$CH_3COOCH_3 + (C_6H_5)_3P \rightarrow (CH_3)$$
$$(C_6H_5)_3P^+(OCOCH_3)^-.$$

It is for this reason that each mol of phosphine, amine, arsine or stibine which may be introduced or fed will be considered as one gram equivalent of cation $A'^{n+}$ in the expression relating to the total amount of halogen $(X_T)$ to that of the cations $A^{m+}$ and $A'^{n+}$ present in the reaction medium.

If a carboxylate of the type defined above is used, the amount thereof is generally such that the molar ration $A'^{n+}/A^{m+}$ ranges from 0.01 to 20. Preferably, this ratio ranges from 0.05 to 10 and more advantageously from 0.1 to 5.

Finally, the presence of hydrogen is required in order to carry out the present process. In general, the hydrogen partial pressure, determined at 25° C., will be at least 0.2 bar, preferably at least 1 bar and even more preferably at least 3 bars. The maximum hydrogen partial pressure which is permitted within the scope of the present invention will depend on the other operating conditions and, to a large extent, on the nature of the intended product (or products). Indeed, if the hydrogen partial pressure is fixed at a value close to the minimum threshold indicated above, the process according to the present invention enables obtainment of acetic anhydride quite efficiently and selectively. On the other hand, in the presence of amounts of hydrogen which are much greater than the threshold which has just been considered, the efficacy of the process is virtually unmodified, but secondary reactions are observed, the most important of which can be represented as follows:

$$CH_3COOCH_3 + CO + H_2 \rightarrow CH_3CHO + CH_3COOH \quad (2)$$

together with the following side reaction:

$$(CH_3CO)_2O + CH_3CHO \rightarrow CH_3CH(OCOCH_3)_2 \quad (3)$$

which results in the formation of ethylidene diacetate from the acetic anhydride and the acetaldehyde, the latter being formed by the secondary reaction (2), these reactions being observed especially at high temperature. However, the various products which can be formed in this case, in addition to the acetic anhydride, are not without value. In fact, ethylidene diacetate is an intermediate in the synthesis of vinyl acetate; the acetic acid can be recycled into the preparation of the methyl acetate, and the acetaldehyde can be hydrogenated to provide ethanol.

In general, the hydrogen partial pressure, measured at 25° C., will not exceed 100 bars; advantageously, it will be less than 70 bars and preferably less than 50 bars.

By the expression "virtually anhydrous reaction medium" there is intended a medium which contains the smallest possible amount of water, taking into account the various industrial constraints. It will be noted, however, that the presence of minor amounts of water, such as those which can be introduced, in the charge or the feed, by technical-grade reactants, can be tolerated.

Also as above indicated, it is necessary for the total amount of halogen compounds present in the reaction medium ($X_T$, expressed in gram atoms of halogen) to be such that the (atomic) ratio $X_T/(m.A^{m+} + n.A'^{n+})$ is less than or equal to 1.

This condition does not exclude the possibility of using halogens ($X_2$), halogen acids (HX), alkyl halides (RX), cobalt halides ($CoX_2$) or ruthenium halides ($RuX_3$), but implies that, if these types of compounds are introduced or fed in, it will be necessary to introduce or feed in either a carboxylate $[A'^{n+}(OCOR)_n^-]$ defined above, or a phosphine, an amine, an arsine or a stibine, in an amount which is at least equivalent to the number of gram atoms of halogen (X) introduced, if appropriate, by means of the abovementioned halogen compounds. It is accepted that, under the reaction conditions, the halogen compounds $X_2$, HX, $CoX_2$ and $RuX_3$ will react with the methyl acetate to produce a methyl halide, which in turn (together with the alkyl halides RX) will react with the phosphine, the amine, the arsine or the stibine to form the corresponding quaternary onium halide.

It is for this reason that, assuming that halogen compounds of the types $X_2$, HX, RX, $CoX_2$ and $RuX_3$ are indeed used, each mol of phosphine, amine, arsine or stibine introduced in order to "neutralize", as it were, these sources of halogen will be considered as one gram equivalent of cation $A^{m+}$ in the expression relating the total amount of halogen ($X_T$) to that of the cations $A^{m+}$ and $A'^{n+}$ present in the reaction medium.

Furthermore, for the same reason as the alkyl halides, (RX), the methyl halide $CH_3X$ can react with the carboxylates $[A'^{n+}(OCOR)_n^-]$ to produce the corresponding ionic halides $(A'^{n+}X_n^-)$.

The phosphines, amines, arsines and stibines to be used, if appropriate, can be represented by the formula (IV) below:

(IV)

in which Q' represents a phosphorus, nitrogen, arsenic or antimony atom and $R_1$ to $R_3$ are as above defined.

It is advantageous to use a phosphine and more particularly triphenylphosphine.

If it is decided to carry out the process according to the invention at a temperature which is above or equal to 160° C., or even above 180° C., it is advantageous to carry out the reaction under a total pressure, at this temperature, which is greater than or equal to 100 bars, and it will be preferable for the initial reaction medium to contain, in addition to the methyl acetate and the various constituents of the subject catalyst system, a solvent selected from among aliphatic carboxylic acids having a maximum of 8 carbon atoms. Among such acids, acetic acid is the preferred. For the process according to the invention to proceed well, the carboxylic acid represents from 1 to 75% by volume of the reaction medium and preferably from 5 to 30% (by volume) of the said medium.

In this case, the initial reaction medium can also contain from 10 to 50% by volume of an additional solvent selected from the group comprising tetramethylenesulfone, N-methylpyrrolidone, monocarboxylic acid amides which are derived from acids having a maximum of 8 carbon atoms and in which the nitrogen atom contains two alkyl substituents having a maximum of 4 carbon atoms, and acetic anhydride.

The carbon monoxide partial pressure, measured at 25° C., is generally greater than 5 bars and preferably greater than 10 bars.

The reaction temperature, which can vary over wide limits, generally ranges from 60° to 300° C. The reaction is advantageously carried out at a temperature ranging from 80° to 240° C. and preferably at a temperature above 100° C., this being the range in which the catalyst system develops optimum efficacy.

One advantage of the present process is the possibility of carbonylating methyl acetate efficiently, even with a low concentration of cobalt, ruthenium and ionic iodide, under a total pressure, at the relevant temperature, on the order of 20 to 300 bars, which is therefore much smaller than that usually recommended for cobalt-based catalyst systems.

Another advantage of the present process is the disappearance of the various constraints associated with the use of the catalyst systems recently proposed for carrying out this carbonylation.

It too is known to the art that methyl acetate, which is the starting material in the present process, can be formed in situ from dimethyl ether; it is therefore also envisaged, within the scope of the present invention, to introduce or feed in dimethyl ether or a mixture of dimethyl ether and ethyl acetate.

Upon completion of the reaction, the products obtained can be easily separated, for example, by fractional distillation of the resulting mixture.

In order to further illustrate the present invention and the advantages thereof, the following specific examples are given, it being understood that same are intended only as illustrative and in nowise limitative.

In the Examples 1 to 35 and also in control experiments (a) to (f) to follow, the procedure employed was as follows:

Methyl acetate, one or more solvents, if appropriate, and the various constituents of the catalyst system were introduced into an autoclave, the nature and the capacity of which being specified below. After the autoclave had been closed, a carbon monoxide pressure and a hydrogen pressure, respectively designated by P(CO) and P(H$_2$) (values measured at 25° C.), were applied.

Shaking by means of a reciprocating system was commenced and the autoclave was then heated to the selected temperature, designated by T, over a period of time of about 25 minutes. The total pressure at this temperature, designated by P(T), was maintained substantially at the indicated value by successively introducing additional amounts of carbon monoxide containing a maximum of 1% (by volume) of hydrogen. After a reaction time designated by t, the autoclave was cooled and degassed. The reaction mixture was then analyzed by chromatography and potentiometry.

The autoclaves used, designated hereafter by A, B and C, respectively have the following characteristics:

A: tantalum autoclave having a capacity of 125 milliliters,

B: Z-8 CNDT 17-12 stainless steel autoclave (AFNOR Standard Specification) having a capacity of 250 milliliters, and C: HASTELLOY B2 autoclave having a capacity of 125 milliliters.

The following abbreviations are used in the examples:
AcOMe: denotes methyl acetate;
AcOH: denotes acetic acid;
$Ac_2O$ : denotes acetic anhydride;
TMS: denotes tetramethylenesulfone;
AcH: denotes acetaldehyde;
EDA: denotes ethylidene diacetate;
Pr: denotes the productivity expressed in grams of the particular product per hour and per liter
meq: means milliequivalent;
mg atoms: means milligram atom;
mmol: means millimol.

All the pressures [P(CO), P($H_2$) and P(T)] are expressed in bars.

EXAMPLES 1 to 9—CONTROL EXPERIMENTS (a) to (d)

Table (I) below summarizes and reports the particular conditions, together with the results obtained, in a first series of experiments carried out utilizing dicobalt octacarbonyl as the source of cobalt, triruthenium dodecacarbonyl as the source of ruthenium and methyltriphenylphosphonium iodide as the ionic iodide; 35 milliliters (ml) of methyl acetate and 10 ml of acetic acid were introduced into autoclave A; 70 ml of methyl acetate and 20 ml of acetic acid were introduced into autoclave B.

Control experiments (a), (c) and (d) evidences that cobalt by itself develops but mediocre carbonylating activity. Control experiment (b) evidences that ruthenium by itself develops virtually no carbonylating activity.

Example 1, in particular, demonstrates the marked efficacy of the process according to this invention.

EXAMPLES 10 to 15—CONTROL EXPERIMENT (e)

Table (II) below summarizes and reports the particular conditions, together with the results obtained, in a second series of experiments carried out in autoclave C on a charge consisting of:

(i) AcOMe: 25 ml;
(ii) AcOH: 5 ml;
(iii) TMS: 15 ml;
(iv) 1 mg atom of cobalt in the form of $Co_2(CO)_8$ (cobalt concentration: 20 mg atoms/l);
(v) 1 mg atom of ruthenium in the form of $Ru_3(CO)_{12}$ (Ru/Co=1);
(vi) 15 mmols of an ionic iodide, the nature of which being specified in Table (II) ($I^-$/Co=15); and
(vii) if appropriate, an alkali metal acetate, the nature and the amount of which being specified in Table (II).

The common operating conditions were as follows:
P(CO)=80 bars
P($H_2$)=10 bars
T=180° C.
P(T)=150 bars
t=120 minutes.

In certain experiments, the amount of methyl iodide present in the reaction medium was determined upon completion of the experiment. This amount, expressed in millimols, is indicated in the column headed ($CH_3I$) in Table (II).

Control experiment (e) was carried out by replacing the ionic iodide by 14 mmols of methyl iodide in the charge.

Control experiment (e) demonstrates the adverse effects of methyl iodide in the subject process.

Examples (11) and (13) evidence the advantage gained by introducing a carboxylate into the reaction medium when using an alkali metal iodide as the ionic iodide.

EXAMPLES 17 to 28—CONTROL EXPERIMENTS (f) and (g)

Table (III) below summarizes and reports the particular conditions, together with the results obtained, in a third series of experiments carried out in autoclave B, using cobalt diacetate tetrahydrate as the source of cobalt (the cobalt concentration was 4.5 mg atoms/l), methyltriphenylphosphonium iodide as the ionic iodide (Example 23 being carried out, however, in the presence of tetraethylammonium iodide) and triruthenium dodecacarbonyl as the source of ruthenium (in Example 18, however, ruthenium acetylacetonate was used), acetic acid being the solvent used. However, in Examples 20 and 21, 20 and 35 ml of acetic anhydride, respectively, were added to the charge; in control experiment (g), 15 mmols of methyl iodide were added to the charge.

The reaction temperature was 210° C. (except in Example 26, where it was 197° C.); P(T) was 250 bars (except in Example 22, where it was only 150 bars). The reaction time, at the relevant temperature was 20 minutes (except in Examples 19 and 20, where it was, respectively, 10 and 25 minutes).

In Example 28, 5 mmols of triphenylphosphine $[X_T/(m.A^{m+}+n.A'^{n+})=0.81]$ were added to the charge.

In control experiment (g), the ratio $X_T/m.A^{m+}+n.A'^{n+})$ was equal to: 1.67.

EXAMPLES 29 to 34

Table IV below summarizes and reports the particular conditions, together with the results obtained, in a fourth series of experiments carried out on a charge comprising:

(i) 20 ml of N-methylpyrrolidine;
(ii) 30 ml of methyl acetate;
(iii) 1.5 mg atoms of cobalt;
(iv) ruthenium (2 mg/atoms in Examples 29 to 33, Ru/Co=1.33; 0.2 mg atom in Example 34, Ru/Co=0.133); and
(v) lithium iodide.

In Examples 30 and 32, 3 mmols of lithium acetate were also introduced. In Example 33, 5 mmols of magnesium acetate were also introduced.

The particular conditions, together with the results obtained, are reported in Table IV below, in which:
Co(OAc)$_2$ denotes cobalt acetate tetrahydrate;
Ru(acac)$_3$ denotes ruthenium acetylacetonate; and
Ru/C denotes ruthenium deposited on charcoal (the total weight of this catalyst was 400 mg).

EXAMPLE 35

In a tantalum autoclave, an experiment was carried out on a charge consisting of:
(i) 30 ml of methyl acetate;
(ii) 20 ml of N-methylpyrrolidone;
(iii) 4.5 mg atoms of cobalt in the form of cobalt acetate tetrahydrate;
(iv) 2 mg atoms of ruthenium in the form of triruthenium dodecacarbonyl (Ru/Co=0.44); and
(v) 9.6 mmols of lanthanum iodide (I$^-$=28.8 meq).
The operating conditions were as follows:
P(CO)=36; P(H$_2$)=7
T=130° C.
P(T)=60
t=155 minutes.

Upon completion of the experiment, the presence of 3.6 g of acetic anhydride was detected by gas phase chromatography.

EXAMPLE 36

The following materials were introduced into a tantalum reactor having a capacity of 125 ml:
(i) 20 ml of N-methylpyrrolidone;
(ii) 30 ml of methyl acetate;
(iii) 1.5 mg atoms of cobalt in the form of cobalt acetate tetrahydrate;
(iv) 2 mg atoms of ruthenium in the form of triruthenium dodecacarbonyl;
(v) 20 mmols of calcium acetate; and
(vi) 40 mmols of methyl iodide.

After the autoclave had been closed, carbon monoxide (35 bars at 25° C.) and hydrogen (7 bars at 25° C.) were introduced. Shaking by means of a reciprocating system was commenced and the autoclave was heated to 70° C. over a period of about 10 minutes. The total pressure at this temperature reached 50 bars and was maintained at this value by successively introducing additional amounts of carbon monoxide containing a maximum of 1% (by volume) of hydrogen. After 190 minutes at this temperature, the autoclave was heated to 120° C. The total pressure at this temperature was 60 bars; it was maintained at this value in the manner indicated above. After 160 minutes at this temperature, the autoclave was cooled and degassed. The reaction mixture was then analyzed by gas phase chromatography. It contained 6.5 g of acetic anhydride.

EXAMPLES 37 to 40—CONTROL EXPERIMENT (h)

In Examples 37 to 40 and also in control experiment (h), the procedure was as follows:
The following materials were introduced into a 300 cm$^3$ stainless steel autoclave equipped with a magnetically driven central stirrer and heated and regulated electrically:
(i) AcOMe: 77 g;
(ii) AcOH: 17.4 g;
(iii) N-methylpyrrolidone: 51.3 g;
(iv) methyltriphenylphosphonium iodide: 50 mmols;
(v) 1.64 mg atoms of cobalt in the form of cobalt diacetate tetrahydrate; and
(vi) 1.64 mg atoms of ruthenium in the form of ruthenium acetylacetonate;
and the autoclave was then heated to a temperature of 200° C., under sweeping with carbon monoxide and hydrogen. The pressure in the autoclave was maintained at 235 bars and the feed rate of the gaseous mixture was 40 l/hour (CNTP). The molar percentage of hydrogen in this feed was maintained constant and is indicated in Table (V) below.

Samples of the reaction mixture were periodically taken and analyzed.

Table (V) below indicates the percentage of hydrogen in the feed by a % of H$_2$; DC of AcOMe is the molar percentage of methyl acetate converted, relative to the amount introduced, respectively, after operating times of 1 hour and 4 hours; Y(Ac$_2$O) is the amount (expressed in molar percentages) of acetic anhydride formed, relative to the amount of methyl acetate converted, after an operating time of four hours; and Y(HYD) is the amount (expressed in molar percentages) of hydrocarbonylation products (AcH and EDA) formed, relative to the amount of methyl acetate converted, after an operating time of 4 hours.

TABLE I

| Example No. | (x) | Cobalt mg atoms | mg atoms/l | Ru mg atoms | Ru/Co | I$^-$ meq | I$^-$/Co | P(CO) | P(H$_2$) | T (°C.) | P(T) | t (minutes) | Ag$_2$O (g) | Pr | EDA (g) | AcH (g) |
|---|---|---|---|---|---|---|---|---|---|---|---|---|---|---|---|---|
| a | A | 1 | 20 | 0 | 0 | 15 | 15 | 130 | 10 | 210 | 250 | 36 | 1.61 | 54 | 0 | 0.08 |
| b | " | 0 | 0 | 1 | " | " | " | " | " | " | " | 35 | 0.39 | 13 | 0 | 0.23 |
| 1 | " | 1 | 20 | 0.5 | 0.5 | " | " | " | " | " | " | 20 | 8.37 | 500 | 0.25 | 0.19 |
| 2 | B | 2 | " | 1 | " | 30 | " | " | " | " | " | " | 17.86 | 535 | 0.57 | 0.54 |
| 3 | " | " | " | 0.04 | 0.02 | " | " | " | " | " | " | 50 | 14.28 | 170 | 1.07 | 0.69 |
| 4 | " | " | " | 0.2 | 0.1 | " | " | " | " | " | " | 33 | 14.90 | 270 | 0.62 | 0.61 |
| 5 | " | " | " | 2 | 1 | " | " | " | " | " | " | 20 | 19.99 | 600 | 0.69 | 0.42 |
| 6 | " | 0.45 | 20 | 1.3 | 2.89 | 15 | 33 | " | " | " | " | " | 25.40 | 760 | 0.47 | 0.67 |
| c | A | 2 | 40 | 0 | 0 | 22.5 | 11.2 | 54 | 4 | 180 | 100 | " | 1.1 | 45 | ND | ND |
| 7 | " | " | " | 1 | 0.5 | " | " | " | " | " | " | " | 3.48 | 140 | " | " |
| d | " | " | " | 0 | 0 | " | " | 39 | 3 | 210 | " | " | 0.58 | 23 | " | " |
| 8 | " | " | " | 1 | 0.5 | " | " | " | " | " | " | " | 2.97 | 120 | " | " |
| 9 | " | " | " | 1 | " | " | " | 135 | 10 | 180 | 250 | " | 6.06 | 240 | " | " |

(x): type of autoclave used
ND: not determined.

TABLE II

| Example No. | $A^{m+}I_m^-$ | $A'^{n+}(OCOCH_3)_n^-$ nature | mmol | $X_T/(m.A^{m+} + n.A'^{n+})$ | $Ac_2O$ (g) | $(CH_3I)$ |
|---|---|---|---|---|---|---|
| e | none | — | 0 | — | 0.3 | 10 |
| 10 | $Li^+I^-$ | — | 0 | 1 | 2.25 | 4.4 |
| 11 | " | $Li^+(OAc)^-$ | 15 | 0.5 | 3.57 | 3.5 |
| 12 | $Na^+I^-$ | — | 0 | 1 | 4.05 | 0.9 |
| 13 | " | $Na^+(OAc)^-$ | 15 | 0.5 | 5.3 | 0.2 |
| 14 | " | " | 60 | 0.2 | 3.57 | " |
| 15 | $K^+I^-$ | — | 0 | 1 | 1.78 | ND |
| 16 | $P^+I^-$ (x) | — | 0 | 1 | 8.3 | 0.2 |

(x): $CH_3(C_6H_5)_3P^+I^-$

TABLE III

| Example No. | AcOMe ml | AcOH ml | Cobalt mg atoms | Ru/Co | $I^-$ meq | $I^-$/CO | P(CO) | $P(H_2)$ | $Ac_2O$ g | $Ac_2O$ Pr | EDA g | EDA Pr | AcH (g) |
|---|---|---|---|---|---|---|---|---|---|---|---|---|---|
| 17 | 70 | 20 | 0.45 | 2.88 | 45 | 100 | 70 | 70 | 11.80 | 350 | 6.33 | 190 | 2.80 |
| 18 | " | " | " | " | " | " | " | " | 11.23 | 335 | 5.52 | 165 | 4.35 |
| 19(+) | " | " | " | " | " | " | " | " | 3.2 | 190 | 1.66 | 100 | 6.2 |
| 20 | 50 | " | " | " | " | " | 105 | " | 21.07 | ~0 | 14.78 | 355 | 2.5 |
| 21 | 35 | " | " | " | " | " | 120 | 20 | 46.19 | 275 | 2.96 | 90 | 0.5 |
| 22 | 70 | 20 | " | " | " | " | 70 | 10 | 10.96 | 330 | ND | ND | ND |
| 23 | " | " | " | " | " | " | 125 | 15 | 16.32 | 490 | ND | " | ND |
| 24 | " | " | " | 0.75 | " | " | 130 | 10 | 10.04 | 300 | " | " | " |
| f | " | " | " | " | " | " | 140 | 0 | 3.0 | 90 | " | " | " |
| 25 | 45 | 0 | 0.23 | 2.87 | 22.5 | 98 | 125 | 15 | 1.94 | 115 | " | " | " |
| 26 | 35 | 10 | " | " | " | " | 70 | 70 | 4.9 | 290 | " | " | " |
| 27 | " | " | " | " | 15 | 65 | 120 | 20 | 10.40 | 620 | " | " | " |
| 28 | " | " | " | " | 22.5 | 98 | " | " | 11.12 | 670 | " | " | " |
| g | " | " | " | " | " | " | 125 | 15 | 2.04 | 120 | " | " | " |

(+): in this experiment, P(T) was maintained constant by introducing additional amounts of a 1/1 (molar) mixture of CO and $H_2$
ND: not determined.

TABLE IV

| Example No. | Cobalt (x) nature | Ruthenium nature | $I^-$ meq | P(CO) | $P(H_2)$ | T °C. | P(T) | t min-utes | $Ac_2O$ g | EDA g |
|---|---|---|---|---|---|---|---|---|---|---|
| 29 | A | $Co_2(CO)_8$ | $Ru_3(CO)_{12}$ | 30 | 32 | 7 | 154 | 60 | 456 | 27 | 0.3 |
| 30 | C | $CoI_2$ | $Ru(acac)_3$ | 67 | 36 | 7 | 125 | 60 | 275 | 6 | ND |
| 31 | A | $Co(OAc)_2$ | $Ru_3(CO)_{12}$ | 70 | 36 | 7 | 120 | 60 | 340 | 22 | 0.15 |
| 32 | A | $CoI_2$ | $Ru_3(CO)_{12}$ | 60 | 40 | 8 | 95 | 60 | 155 | 1.3 | ND |
| 33 | A | $Co(OAc)_2$ | $Ru_3(CO)_{12}$ | 40 | 19 | 3 | 120 | 30 | 405 | 10.7 | ND |
| 34 | A | $Co_2(CO)_8$ | Ru/C | 30 | 32 | 7 | 154 | 60 | 375 | 18.5 | 0.17 |

(x): type of autoclave used.
ND: not determined.

TABLE V

| Example No. | % of $H_2$ | DC of ACOMe 1 hour | DC of ACOMe 4 hours | $Y(Ac_2O)$ | Y(HYD) |
|---|---|---|---|---|---|
| h | 0 | 16 | 35 | 100 | 0 |
| 37 | 1 | 31 | 78 | 100 | 0 |
| 38 | 2 | 51 | 95 | 99.4 | 0.6 |
| 39 | 5 | 59 | 96 | 94 | 6 |
| 40 | 10 | 59 | 97 | 84 | 16 |

While the invention has been described in terms of various preferred embodiments, the skilled artisan will appreciate that various modifiations, substitutions, omissions, and charge may be made without departing from the spirit thereof. Accordingly, it is intended that the scope of the present invention be limited solely by the scope of the following claims.

What is claimed is:

1. In a process for the carbonylation of method acetate to produce acetic anhydride in homogeneous liquid phase, the improvement which comprises conducting such carbonylation in a virtually anhydrous medium, in the presence of:
   (a) a cobalt source;
   (b) a ruthenium source;
   (c) an ionic iodide of the formula:

$$A^{m+}I_m^-$$

in which $A^{m+}$ is a nitrogen group quaternary onium cation, an alkali metal cation, an alkaline earth metal cation, a cation of a lanthanide group metal or a cation of an actinide group metal, with m being 1, 2, 3 or 4; and
   (d) hydrogen, as an amount of at least about 1 mole percent of the combined gases hydrogen and carbon monoxide;
   with the total amount of halogen compounds present in the reaction medium, expressed in gram atoms of halogen and designated as $X_T$, being such that the atomic ratio $X_T/(m \cdot A^{m+})$ is less than or equal to 1.

2. In a process for the carbonylation of methyl acetate to produce acetic anhydride in homogeneous liquid phase, the improvement which comprises conducting such carbonylation in a virtually anhydrous medium, in the presence of:
   (a) a cobalt source;
   (b) a rutheium source;

(c) an ionic iodide of the formula:

in which $A^{m+}$ is a nitrogen group quaternary onium cation, an alkali metal cation, an alkaline earth metal cation, a cation of a lanthanide group metal or a cation of an actinide group metal, with m being 1, 2, 3 or 4;

(c') a carboxylate of the formula:

in which n is 1, 2, 3 or 4 and $A'^{n+}$ is defined as was $A^{m+}$, with $A'^{n+}$ and $A^{m+}$ being the same or different, an R is an alkyl, aralkyl or aryl radical having a maximum of 8 carbon atoms; and (d) hydrogen, as an amount of at least about 1 mole percent of the combined gases hydrogen and carbon monoxide;

with the total amount of halogen compounds present in the reaction medium, expressed in gram atoms of halogen and designated by $X_T$, being such that the atomic ratio $X_T/(.A^{m+}+n.A'^{n+})$ is less than or equal to 1.

3. The process as defined by claims 1 or 2, wherein the hydrogen partial pressure, measured at 25° C., is greater than or equal to 0.2 bar.

4. The process as defined by claims 1 or 2, wherein the carbon monoxide partial pressure, measured at 25° C., is greater than or equal to 5 bars.

5. The process as defined by claims 1 or 2, wherein the reaction temperature ranges from 60° to 300° C.

6. The process as defined by claims 1 or 2, wherein the cobalt concentration ranges from 0.1 to 200 mg atoms/l.

7. The process as defined by claim 3, wherein the hydrogen partial pressure, measured at 25° C., is less than 100 bars.

8. The process as defined by claim 6, wherein the molar ratio $I^-/Co$ is greater than or equal to 5.

9. The process as defined by claim 8, wherein the molar ratio $I^-/Co$ ranges from 15 to 150.

10. The process as defined by claim 8, wherein the atomic ratio Ru/Co ranges from 0.005 to 25.

11. The process as defined by claim 10, wherein the atomic ratio Ru/Co ranges from 0.2 to 5.

12. The process as defined by claim 10, wherein the ionic iodide is a quaternary phosphonium or quaternary ammonium iodide.

13. The process as defined by claim 10, wherein the ionic iodide is an alkali metal iodide, an alkaline earth metal iodide, an iodide of a lanthanide group metal or an iodide of an actinide group metal.

14. The process as defined by claim 13, wherein the ionic iodide is an alkali metal iodide.

15. The process as defined by claim 14, wherein the ionic iodide is lithium iodide.

16. The process as defined by claim 2, wherein the molar ratio $A'^{n+}/A^{m+}$ ranges from 0.01 to 20.

17. The process as defined by claim 13, wherein the reaction is carried out at a temperature below 160° C., under a total pressure, at such temperature, of less than 100 bars, and in a tetramethylenesulfone, N-methylpyrrolidone or monocarboxylic acid amide solvent, such amide solvent being derived from an acid having a maximum of 8 carbon atoms, and in which the nitrogen atom contains two alkyl substituents having a maximum of 4 carbon atoms.

18. The process as defined by claims 1 or 2, wherein the reaction is carried out at a temperature which is above or equal to 160° C. and under a total pressure, at such temperature, which is greater than or equal to 100 bars.

19. The process as defined by claim 18, wherein the reaction medium comprises an aliphatic carboxylic acid solvent having a maximum of 8 carbon atoms.

20. The process as defined by claim 19, said solvent being acetic acid.

* * * * *